(12) United States Patent
Shimomura et al.

(10) Patent No.: US 6,180,626 B1
(45) Date of Patent: *Jan. 30, 2001

(54) VASCULAR-PERMEABILITY SUPPRESSANTS

(75) Inventors: Kyoichi Shimomura, Suita; Toshitaka Manda; Fusako Nishigaki, both of Osaka, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/051,086

(22) PCT Filed: Oct. 11, 1996

(86) PCT No.: PCT/JP96/02945

§ 371 Date: Apr. 13, 1998

§ 102(e) Date: Apr. 13, 1998

(87) PCT Pub. No.: WO97/13509

PCT Pub. Date: Apr. 17, 1997

(30) Foreign Application Priority Data

Oct. 11, 1995 (JP) .................................................. 7-263363
Oct. 24, 1995 (JP) .................................................. 7-276004

(51) Int. Cl.⁷ ........................ A61K 31/535; A61K 31/54; A61K 31/495; A61K 31/47; A61K 31/445
(52) U.S. Cl. ..................................... 514/231.5; 514/227.8; 514/255; 514/314; 514/326; 514/336; 514/422; 514/475
(58) Field of Search ................................. 514/231.5, 255, 514/314, 326, 336, 422, 475, 227.8

(56) References Cited

U.S. PATENT DOCUMENTS

| | | | |
|---|---|---|---|
| 5,164,410 | 11/1992 | Kishimoto et al. | 514/475 |
| 5,166,172 | 11/1992 | Kishimoto et al. | 514/475 |
| 5,767,293 | * 6/1998 | Oku et al. | 549/332 |
| 5,789,405 | * 8/1998 | Oku et al. | 514/227.8 |

FOREIGN PATENT DOCUMENTS 0 354 787  2/1990 (EP) .

OTHER PUBLICATIONS

Tsuijmoto, H., et al., "Therapeutic effects of the angiogenesis inhibitor TNP–470 against carcinomatous peritonitis in mice" *Anti–Cancer Drugs*, vol. 6, No. 3, pp. 438–442 (1995).

Ahmed, M., et al., "The Angiogenesis Inhibitor TNP–470 (AGM–1470) Improves Long–Term Survival of Rats with Liver Metastis," *Journ. of Surg. Research*, vol. 64, No. 1, pp. 35–41 (1996).

Ferrara, N., "The role of vascular endothelial growth factor in pathological angiogenesis," *Breast Cancer Research And Treatment*, vol. 36, No. 2, pp. 127–137 (1995).

Garrison, R., et al., "Mechanisms of Malignant Ascites Production," *Journ. of Surg. Research*, vol. 42, No. 2, pp. 126–132 (1987).

\* cited by examiner

*Primary Examiner*—Kevin E. Weddington
(74) *Attorney, Agent, or Firm*—Oblon, Spivak, McClelland, Maier & Neustadt, P.C.

(57) ABSTRACT

A vascular permeability suppressant includes an oxaspirooctane derivative of the general formula (I):

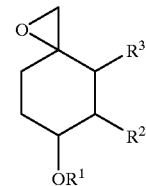

[wherein, $R^1$ represents, for example, lower alkylcarbamoyl group or protected carbamoyl group, $R^2$ represents lower alkoxyl group, and $R^3$ represents the formula:

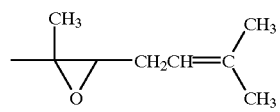

or a pharmaceutically acceptable salt thereof, together with a pharmaceutically acceptable carrier. Particularly, for example, an agent that can prevent retention of carcinomatous pleural effusion or carcinomatous ascites.

15 Claims, No Drawings

VASCULAR-PERMEABILITY SUPPRESSANTS

TECHNICAL FIELD

This invention relates to a novel vascular permeability suppressants, more particularly a vascular permeability suppressant which prevents retention of carcinomatous pleural effusion or carcinomatous ascites through their suppressing action on vascular permeability, and to an agent which prevents carcinomatous pleural effusion or carcinomatous ascites retention, and also to the method of suppressing retention of carcinomatous pleural effusion or carcinomatous ascites by utilizing this agent.

PRIOR ART

Oxaspirooctane derivatives of the general formula (I):

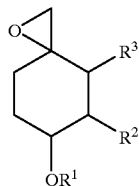

wherein, $R^1$ represents carbamoyl group; lower alkylcarbamoyl group; hydroxy(lower)alkylcarbamoyl group; lower alkoxy(lower)alkylcarbamoyl group; lower alkylthio(lower)alkylcarbamoyl group; lower alkoxycarbonyl(lower)alkylcarbamoyl group; lower alkylcarbamoyloxy(lower)alkylcarbamoyl group; di(lower)alkylcarbamoyl group; N-[hydroxy(lower)alkyl](lower)alkylcarbamoyl group; N-[hydroxy(lower)alkyl](lower)alkylcarbamoyloxy(lower)alkylcarbamoyl group; lower alkylcarbamoyloxy(lower)alkenoyl group; N-[heterocyclic carbonyloxy(lower)alkyl](lower)alkylcarbamoyl group; cyclo(lower)alkylcarbamoyl group; arylcarbamoyl group; haloarylcarbamoyl group; protected carbamoyl group; lower alkylthiocarbamoyl group; heterocyclic carbamoyl group; ar(lower)alkenoyl group; lower alkoxycarbonyl group; heterocyclic carbonyl group which may have lower alkyl group, hydroxyl group, hydroxy(lower)alkyl group, lower alkoxy(lower)alkyl group, or lower alkoxycarbonyl group; lower alkyl group; carboxy(lower)alkyl group; protected carboxy(lower)alkyl group; ar(lower)alkyl group which may have halogen atom or lower alkoxyl group: heterocyclic(lower)alkyl group; lower alkylcarbamoyl(lower)alkyl group; hydroxy(lower)alkenoyl group; acyloxy(lower)alkenoyl group or diacyloxy(lower)alkenoyl group; $R^2$ represents lower alkoxyl group, and $R^3$ represents the formula:

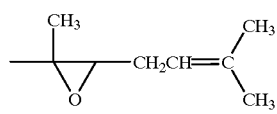

the formula:

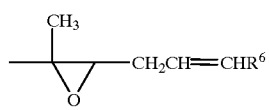

(wherein $R^6$ represents protected carboxyl group), the formula:

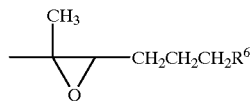

(wherein $R^6$ represents the same as described above), the formula:

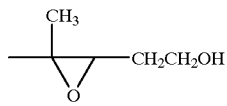

the formula:

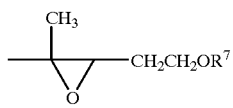

(wherein $R^7$ represents protected carboxy(lower)alkyl group or ar(lower)alkyl group which may have halogen atom), or the formula:

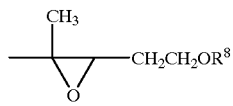

(wherein $R^8$ represents acyl group), and the process for the production thereof are publicly known as described in Japanese Patent Gazette (Kokai) No. (Hei)2-85272.

The angiogenesis-suppressing activity of the above-mentioned oxaspirooctane derivatives (I) are known as described in Japanese Patent Gazette (Kokai) No. (Hei)2-85272.

Medicines that suppress vascular permeability itself or medicines that prevent the pathological condition that can occur as the result of increased vascular permeability, for example serious symptoms due to retention of carcinomatous ascites or pleural effusion, have not yet been known. Therefore, patients with increased retention of carcinomatous ascites or pleural effusion are inevitably treated only with passive means such as removal of ascites or pleural effusion with a syringe, etc., and thus vascular permeability suppressants serving as agents which actively suppress ascites retention or pleural effusion itself have been desired. The present inventors discovered in the result of their researches that oxaspirooctane derivatives (I) have an excellent suppressing effect on vascular permeability and that they also prevent retention of carcinomatous ascites or carcinomatous pleural effusion based on the said effect. Thus the inventors completed the present invention after extensive researches.

DISCLOSURE OF THE INVENTION

This invention is concerned with a vascular permeability suppressant, such as agents which prevent retention, for example, of carcinomatous pleural effusion or carcinomatous ascites, contain an oxaspirooctane derivative (I) represented by the above-mentioned chemical formula or a pharmaceutically acceptable salt thereof as the active ingredient.

The said pharmaceutically acceptable salts are exemplified by pharmaceutically acceptable conventional salts such as sodium salts, ammonium salts, and the like.

BEST EMBODIMENTS OF THE INVENTION

The substituents of an oxaspirooctane derivative (I) as the active ingredient of the vascular permeability suppressant of this invention, are defined in the following.

"Lower" means the carbon atom number 1 to 6 unless otherwise indicated.

Preferable "lower alkyl groups" in "lower alkylcarbamoyl group", "hydroxy(lower)alkylcarbamoyl group", "lower alkoxy(lower)alkylcarbamoyl group", "lower alkylthio (lower)alkylcarbamoyl group", "lower alkoxycarbonyl (lower)alkylcarbamoyl group", "lower alkylcarbamoyl (lower)alkylcarbamoyl group", di(lower)alkylcarbamoyl group", "ar(lower)alkyl group", "N-[hydroxy(lower)alkyl] (lower)alkylcarbamoyl group", "N-[hydroxy(lower)alkyl] (lower)alkylcarbamoyloxy(lower)alkylcarbamoyl group", "lower alkylcarbamoyloxy(lower)alkenoyl group", "lower alkylthiocarbamoyl group", "lower alkyl group", "hydroxy (lower)alkyl group", "lower alkoxy(lower)alkyl group", "carboxy(lower)alkyl group", "protected carboxy(lower) alkyl group", "heterocyclic(lower)alkyl group", or "lower alkylcarbamoyl(lower)alkyl group" may include methyl group, ethyl group, propyl group, isopropyl group, butyl group, isobutyl group, t-butyl group, pentyl group, hexyl group, etc.

Preferable "lower alkoxyl groups" in "lower alkoxy (lower)alkylcarbamoyl group", "lower alkoxycarbonyl (lower)alkylcarbamoyl group", "lower alkoxycarbonyl group", and "lower alkoxy(lower)alkyl group" may include methoxy group, ethoxy group, propoxy group, butoxy group, pentyloxy group, hexyloxy group, etc.

Preferable "lower alkylthio groups" in "lower alkylthio (lower)alkylcarbamoyl group" may include methylthio group, ethylthio group, propylthio group, butylthio group, pentylthio group, hexylthio group, etc.

Preferable "lower alkenoyl groups" in "lower alkylcarbamoyloxy(lower)alkenoyl group", "hydroxy (lower)alkenoyl group", "acyloxy(lower)alkenoyl group", "diacyloxy(lower)alkenoyl group" and "ar(lower)alkenoyl group" may include $C_3$–$C_6$ alkenoyl groups such as acryloyl group, crotonoyl group, etc.

Preferable "cyclo(lower)alkylcarbamoyl group" is "cylco ($C_3$–$C_7$)alkylcarbamoyl group", including cyclopropylcarbamoyl group, cyclobutylcarbamoyl group, cyclopentylcarbamoyl group, cyclohexylcarbamoyl group, cycloheptylcarbamoyl group, etc.

Preferable "aryl groups" in "arylcarbamoyl group", "haloarylcarbamoyl group", "ar(lower)alkyl group", and "ar (lower)alkenoyl group" may include phenyl group, tolyl group, xylyl group, naphthyl group, etc.

Preferable halogens in "haloaryl group" and "halogen" may include chlorine, bromine, iodine, and fluorine.

Preferable "heterocycles" in "N-[heterocyclic carbonyloxy(lower)alkyl](lower)alkylcarbamoyl group", "heterocyclic carbonyl group", "heterocyclic carbamoyl group", and "heterocyclic(lower)alkyl group" may include mono-ring heterocycles containing nitrogen atom as the heteroatom (e.g. pyridyl group, pyrrolidyl group, piperidyl group, piperazinyl group, 2-oxopyrrolidyl group, etc.), mono-ring heterocycles containing nitrogen and oxygen atoms as the heteroatoms (e.g. morpholinyl group, etc.), mono-ring heterocycles containing nitrogen and sulfur atoms as the heteroatoms (e.g. thiomorpholinyl group, etc.), benzene- condensed heterocycles containing nitrogen atom as the heteroatom (e.g. quinolyl group etc.), and the like.

Preferable "protected carbamoyl group" means carbamoyl group protected with a conventional carbamoyl-protecting group such as halo(lower)alkanoyl group exemplified by trichloroacetyl group, dichloroacetyl group, and monochloroacetyl group.

Preferable "protected carboxyl groups" in "protected carboxy(lower)alkyl group" and "protected carboxyl group" may include esterified carboxyl groups such as lower alkoxycarbonyl groups (e.g. methoxycarbonyl group, ethoxycarbonyl group, propoxycarbonyl group, isopropoxycarbonyl group, butoxycarbonyl group, pentyloxycarbonyl group, hexyloxycarbonyl group, etc.), and the like.

Preferable "acyl groups" in "acyloxy(lower)alkenoyl group" and "diacyloxy(lower)alkenoyl group" may include lower alkanoyl group (e.g. formyl group, acetyl group, propionyl group, etc.), aroyl group (e.g. benzoyl group), lower alkanesulfonyl group (e.g. methanesulfonyl group, ethanesulfonyl group, etc.), and the like.

Among the oxaspirooctane derivatives (I) having the groups exemplified above, more preferable ones are compounds having lower alkylcarbamoyl group or protected carbamoyl group for $R^1$, lower alkoxyl group for $R^2$, and the group represented by the formula:

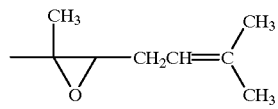

for $R^3$.

The most preferable compounds are exemplified by:

6-methylcarbamoyloxy-5-methoxy-4-[2-methyl-3-(3-methyl-2-butenyl)oxiranyl]-1-oxaspiro[2.5]octane, and 6-monochloroacetylcarbamoyloxy-5-methoxy-4-[2-methyl-3-(3-methyl-2-butenyl)oxiranyl]-1-oxaspiro[2.5]octane, etc.

The dosage form of the vascular permeability suppressant or the agent which suppresses retention, for example, of carcinomatous pleural effusion or carcinomatous ascites based on the said suppressing effect provided by this invention is not particularly specified, but the agents are provided in various dosage forms including capsules, tablets, granules, powders, buccal preparations, sublingual preparations, liquid preparations, etc. with pharmaceutically acceptable carriers combined. These pharmaceutical preparations are orally or parenterally administered to mammals including man.

The pharmaceutically acceptable carriers may include various organic and inorganic carriers conventionally used for formulation. That is, fillers (e.g. sucrose, starch, mannitol, sorbitol, lactose, glucose, cellulose, talc, calcium phosphate, calcium carbonate, etc.), binders (cellulose, methylcellulose, hydroxypropylcellulose, polypropyl pyrrolidone, gelatin, acacia, polyethylene glycol, sucrose, startch, etc.), disintegrators (starch, carboxymethylcellulose, calcium carboxymethylcellulose, hydroxypropyl starch, sodium glycol starch, sodium hydrogencarbonate, calcium phosphate, calcium citrate, etc.), lubricants (e.g. magnesium stearate, aerosil, talc, sodium lauryl sulfate, etc.), flavors (e.g. citric acid, menthol, glycine, orange powder, etc.), preservatives (e.g. sodium benzoate, sodium bisulfate, methylparaben, propylparaben, etc.), stabilizers (e.g. citric acid, sodium citrate, acetic acid, etc.), suspending agents (e.g. methylcellulose, polyvinyl pyrrolidone, aluminum stearate, etc.), distributing agents (e.g. surfactants, etc.), aqueous diluents (e.g. water), oils (sesame oil, etc.), and base wax (e.g. cacao butter, polyethylene glycol, white soft paraffin, etc.) can be used.

The dose of an oxaspirooctane derivative (I) may depend on kinds of the compound (I) as well as other various factors including the nature of the underlying disease causing increased vascular permeability, for example the nature and the site of cancer, body weight and/or age of the patient, and administration route. The preferable dose may be selected normally from the range of 0.01 to 10 mg/kg/day for injection and 0.5 to 50 mg/kg/day for oral administration.

The invention will be more clearly understood with reference to the following Test Examples.

TEST EXAMPLE 1

(1) Test Compound

6-Methylcarbamoyloxy-5-methoxy-4-[2-methyl-3-(3-methyl-2-butenyl)oxiranyl]-1-oxaspiro[2.5]octane (2) Formulation a. Sustained Release Preparation

TABLE 1

| Ingredient | Amount combined (g) | |
| --- | --- | --- |
|  | Preparation of the invention | Placebo preparation |
| Test compound | 1.00 | 0.00 |
| LGA-5010 (Note 1) | 5.00 | 5.00 |
| Carplex (Note 2) | 0.04 | 0.04 |

(Note 1): A biodegradable polymer compound obtained from reaction of lactic acid and glycolic acid (Wako Pure Chemical Industries, LTD.)
(Note 2): Silicone dioxide hydrate (Shionogi & Co., Ltd.)

The sustained release preparation was stored in a freezer.

b. Vehicle

TABLE 2

| Ingredient | Amount combined (g) |
| --- | --- |
| aluminum stearate | 3.0 |
| sesame oil | 97.0 |

The vehicle was stored at room temperature.

Immediately before administration to test animals, the above-mentioned sustained release preparation (60.4 mg: corresponding to 10 mg of the test compound in the preparation of this invention) was added to the above-mentioned vehicle (20 ml) and the mixture was slightly stirred with a spatula, to give a suspension.

(3) Tumor Cells and Preparation of Cells for Implantation in Test Animals

Tumor cells used were Meth A fibrosarcoma (mouse fibrosarcoma), and subcultured every 7 days in the peritoneal cavity of BALB/c strain mouse. The resultant Meth A cells were washed with Hanks' solution, and suspended in Hanks' solution. The viable cells were counted with the Trypan blue dye exclusion method. Cell preparations of $5 \times 10^6$ cells/ml and of $1.25 \times 10^7$ cells/ml were made for intrathoracic implantation and for intraperitoneal implantation in the test animals.

(4) Administration Schedule a. Effect on Retention of Carcinomatous Pleural Effusion BALB/c strain mice were divided into two groups (6 animals per group), and Meth A cells ($5 \times 10^5$ cells/0.1 ml/mouse) were implanted into the thoracic cavity of each mouse. To animals of one group was subcutaneously administered the preparation of this invention (10 mg/kg) on 3 occasions, i.e. on the day of implantation, 2 days later, and 4 days later. To the animals of the other group was administered the placebo preparation according to the same dosing schedule. Six days after implantation of the tumor cells, pleural effusion was obtained.

b. Effect on Retention of Carcinomatous Ascites

BALB/c strain mice were divided into two groups (6 animals per group), and Meth A cells ($2.5 \times 10^6$ cells/0.2 ml/mouse) were implanted into the peritoneal cavity of each mouse. To animals of one group was subcutaneously administered the preparation of this invention (10 mg/kg) on 3 occasions, i.e. on the day of implantation, 2 days later, and 4 days later. To the animals of the other group was administered the placebo preparation according to the same dosing schedule. Seven days after implantation of the tumor cells ascites was obtained.

(5) Test Results a. Effect on Retention of Carcinomatous Pleural Effusion

The amount of the pleural effusion obtained was measured. Then the cells in the thoracic cavity (including tumor cells) were removed by centrifugation, and the volume of the pleural effusion after removal of the cells was measured. The results are shown in Table 3. Each value is the mean ±S.E. In the Table, the number of mice in the placebo-treated group is 2 because, as described below, 4 of 6 mice died so that only the data of the remaining 2 animals could be obtained.

TABLE 3

| | | Pleural effusion retained (ml) | |
| --- | --- | --- | --- |
| Treatment group | Number of mice | including cells in thoracic cavity | Without cells in thoracic cavity |
| Placebo preparation | 2 | 1.1 ± 0 | 0.7 ± 0.1 |
| Preparation of this invention | 6 | 0.4 ± 0.1** | 0.2 ± 0.1* |

*p < 0.05 vs placebo    **p < 0.01 vs placebo
(Student's t test when the variance is equal, Aspin-Welch's t test when the variance is not equal)

The total amount of retained pleural effusion (including the cells) was 1.1 ml in the placebo-treated group and 0.4 ml in the group treated with the preparation of this invention, demonstrating the significant pleural effusion retention-suppressing effect of the preparation of this invention. The amount of pleural effusion after removal of the cells in the thoracic cavity was 0.7 ml in the placebo-treated group and 0.2 ml in the group treated with the preparation of this invention, demonstrating again the significant pleural effusion retention-suppressing effect of the preparation of this invention.

Four of the 6 animals of the placebo group died but no animals died in the group treated with the preparation of this invention, indicating a significant life-prolonging effect of the preparation of this invention.

b. Effect on Retention of Carcinomatous Ascites

The amount of the ascites obtained was measured. Then the cells from the peritoneal cavity (including tumor cells)

were removed by centrifugation, and the volume of the ascites after removal of the cells was measured. The results are shown in Table 4. Each value is the mean ±S.E. No mice died in this experiment.

TABLE 4

| Treatment group | Number of mice | Ascites retained (ml) | |
|---|---|---|---|
| | | including cells in peritoneal cavity | without cells in peritoneal cavity |
| Placebo preparation | 6 | 3.5 ± 0.3 | 2.2 ± 0.2 |
| Preparation of this invention | 6 | 1.0 ± 0.1** | 0.5 ± 0.1** |

**$p < 0.01$ vs placebo
(Student's t test when the variance is equal, Aspin-Welch's t test when the variance is not equal)

The total amount of retained ascites (including the cells) was 3.5 ml in the placebo-treated group and 1.0 ml in the group treated with the preparation of this invention, demonstrating the significant ascites retention-suppressing effect of the preparation of this invention. The amount of ascites after removal of the cells in the peritoneal cavity was 2.2 ml in the placebo group and 0.5 ml in the group treated with the preparation of this invention, demonstrating again the significant ascites retention-suppressing effect of the preparation of this invention.

TEST EXAMPLE 2

(1) Test Compound

6-Monochloroacetylcarbamoyloxy-5-methoxy-4-[2-methyl-3-(3-methyl-2-butenyl)oxiranyl]-1-oxaspiro [2.5]octane (2) Formulation For the preparation of this invention, was used the solution of 86.0 mg of the test compound in 3.0 ml of propyleneglycol contained in a minipump (Note 1). For the placebo preparation, was used only the above-mentioned propyleneglycol contained in a minipump. Note 1: AZLET Mini-Osmotic Pump Model 2001: This can release a medicine solution continuously for 7 days at the mean pumping rate of 1.0 μl/hour.

(3) Tumor Cells and Preparation of Cells for Intrathoracic Implantation in Test Animals The cells were prepared under the same conditions as those for Test Example 1.

(4) Treatment Schedule for Investigating the Suppressing Effect on Retention of Carcinomatous Pleural Effusion BALB/c strain mice were divided into 2 groups (5 animals per group), Meth A cells ($5 \times 10^5$ cells/0.1 ml/mouse) were implanted in the thoracic cavity of each animal. The preparation of this invention contained in the above-mentioned minipump was implanted subcutaneously on the day of the implantation in one group, while the placebo preparation was administered in the other group according to the same schedule. In the group treated with the preparation of this invention, the animals received the test compound at the dose of 32 mg/kg/day. Five days after implantation of the tumor, the pleural effusion was obtained.

(5) Test Results

The measurement was made with the same method as in Test Example 1. The results are shown in Table 5. Each value is mean ±S.E.

TABLE 5

| Treatment group | Number of mice | Pleural effusion retained (ml) | |
|---|---|---|---|
| | | including cells in thoracic cavity | without cells in thoracic cavity |
| Placebo preparation | 5 | 0.7 ± 0.1 | 0.5 ± 0.1 |
| Preparation of this invention | 5 | 0.1 ± 0.0* | 0.1 ± 0.0* |

*$p < 0.05$ vs placebo
(Student's t test when the variance is equal, Aspin-Welch's t test when the variance is not equal)

The total amount of retained pleural effusion (including the cells) was 0.7 ml in the placebo preparation treated group and 0.1 ml in the group treated with the preparation of this invention, demonstrating the significant pleural effusion retention-suppressing effect of the preparation of this invention. The amount of pleural effusion after removal of the cells in the thoracic cavity was 0.5 ml in the placebo group and 0.1 ml in the group treated with the preparation of this invention, demonstrating again the significant pleural effusion retention-suppressing effect of the preparation of this invention.

TEST EXAMPLE 3

(1) Test Compound

The same compound as in Test Example 2.

(2) Formulation

For the preparation of this invention, was used the solution of 105 mg of the test compound in 6.0 ml of physiological saline containing 10% polyoxyethylene hydrogenated castor oil (HCO-60). For the placebo preparation, was used the above-mentioned physiological saline containing only 10% polyoxyethylene hydrogenated castor oil.

(3) Preparation of Tumor Cells and of Tumor Cell-derived Vascular Permeability Promoter Tumor cells used were Meth A fibrosarcoma (mouse fibrosarcoma) prepared by subculture under the same conditions as for Test Example 1, and implanted in mice. From mice 6 days after implantation, ascites was obtained, and the supernatant of the ascites after removal of tumor cells (2000 rpm, 10 min.) was used as the tumor cells-derived vascular permeability promoter.

(4) Administration Schedule

Hartley strain guinea pigs were divided into 2 groups (4 animals per group), and the preparation of this invention was administered subcutaneously in one group (dose: 32 mg/kg). In the other group, the placebo preparation of the same volume was administered subcutaneously. One hour after administration, 1 ml of the solution of Evans blue in physiological saline (10 mg/ml) was injected intravenously, followed by immediate subcutaneous administration of 0.1 ml of the ascites supernatant. Thirty minutes later the skin of each guinea pig with leakage of Evans blue was sampled, and soaked in 1 ml of 0.1N-KOH overnight to be solubilized. After solubilization, 4 ml of acetone-2.5N phosphoric acid mixture (17:3) was added to extract Evans blue, and $OD_{620}$ of the extract was determined.

(5) Test Results

The results of determination of $OD_{620}$ of the extract are shown in Table 6. Each value is the mean ±S.E.

TABLE 6

| Treatment group | Number of mice | $OD_{620}$ |
| --- | --- | --- |
| Placebo preparation | 4 | $0.117 \pm 0.009$ |
| Preparation of this invention | 4 | $0.082 \pm 0.003*$ |

*$p < 0.05$ vs placebo
(Student's t test when the variance is equal, Aspin-Welch's t test when the variance is not equal)

The $OD_{620}$ value in the placebo group was 0.117 whereas the value was 0.082 in the group treated with the preparation of this invention, clearly showing that the leakage of Evans blue through the vessels was significantly decreased after administration of the preparation of this invention. That is, it was demonstrated that the preparation of this invention can significantly suppress the vascular permeability-promoting effect ascribable to the tumor cells-derived vascular permeability promoter.

Industrial Applicability

This invention is constituted as described above, and therefore can provide vascular permeability suppressants, particularly agents that can prevent retention of carcinomatous pleural effusion or carcinomatous ascites.

What is claimed is:

1. A method for suppressing vascular permeability in mammals comprising administering to a mammal in need thereof a vascular permeability suppression effective amount of an oxaspirooctane derivative of the general formula (I):

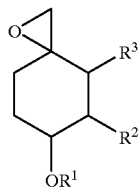

wherein, $R^1$ represents carbamoyl group; lower alkylcarbamoyl group; hydroxy(lower)alkylcarbamoyl group; lower alkoxy(lower)alkylcarbamoyl group; lower alkylthio(lower) carbamoyl group; lower alkoxycarbonyl(lower) alkylcarbamoyl group; lower alkylcarbamoyloxy(lower) alkylcarbamoyl group, di(lower)alkylcarbamoyl group; N-{hydroxy(lower)alkyl}(lower)alkylcarbamoyl group; N-{hydroxy(lower)alkyl}(lower)alkylcarbamoyloxy(lower) alkylcarbamoyl group; lower alkylcarbamoyloxy(lower) alkenoyl group; N-{heterocyclic carbonyloxy(lower)alkyl} (lower)alkylcarbamoyl group; cyclo(lower)alkylcarbamoyl group; arylcarbamoyl group; haloarylcarbamoyl group; protected carbamoyl group; lower alkylthiocarbamoyl group; heterocyclic carbamoyl group; ar(lower)alkenoyl group; lower alkoxycarbonyl group; heterocyclic carbonyl group which may have lower alkyl group, hydroxyl group, hydroxy(lower)alkyl group, lower alkoxy(lower)alkyl group, or lower alkoxycarbonyl group; lower alkyl group; carboxy(lower)alkyl group; protected carboxy(lower)alkyl group; ar(lower)alkyl group which may have halogen atom or lower alkoxyl group; heterocyclic(lower)alkyl group; lower alkylcarbamoyl(lower)alkyl group; hydroxy(lower) alkenoyl group; acyloxy(lower)alkenoyl group or diacyloxy (lower)alkenoyl group; $R^2$ represents lower alkoxyl group, and $R^3$ represents the formula:

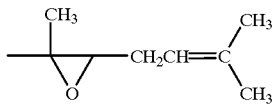

the formula:

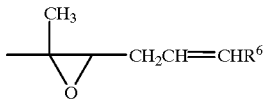

(wherein $R^6$ represents protected carboxyl group), the formula:

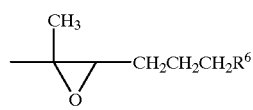

(wherein $R^6$ represents the same as described above), the formula:

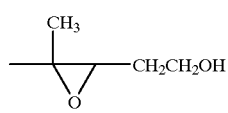

the formula:

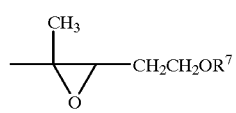

(wherein $R^7$ represents protected carboxy(lower)alkyl group or ar(lower)alkyl group which may have halogen atom), or the formula:

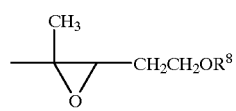

(wherein $R^8$ represents acyl group), or a pharmaceutically acceptable salt thereof.

2. The method of claim 1, wherein $R^1$ represents lower alkylcarbamoyl group, $R^2$ represents lower alkoxyl group, and $R^3$ represents the formula:

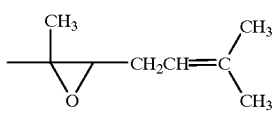

in general the formula of oxaspirooctane derivative (I).

3. The method of claim 2, wherein the oxaspirooctane derivative (I) is 6-methylcarbamoyloxy-5-methoxy-4-{2-methyl-3-methyl-2-butenyl)oxiranyl}-1-oxaspiro{2.5}octane.

4. The method of claim 1, wherein R¹ represents protected carbamoyl group, R² represents lower alkoxyl group, and R³ represents the formula:

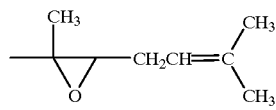

in the general formula of the oxaspirooctane derivative (I).

5. The method of claim 4, wherein the oxaspirooctane derivative (I) is 6-monochloroacetylcarbamoyloxy-5-methoxy-4-{2-methyl-3-(3-methyl-2-butenyl)oxiranyl}-1-oxaspiro{2.5}octane.

6. A method for suppressing retention of carcinomatous pleural effusion in mammals, comprising administering to a mammal in need thereof a carcinomatous pleural effusion retention suppression effective amount of an oxaspirooctane derivative of the general formula (I):

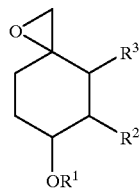

wherein, R¹ represents carbamoyl group; lower alkylcarbamoyl group; hydroxy(lower)alkylcarbamoyl group; lower alkoxy(lower)alkylcarbamoyl group; lower alkylthio(lower)carbamoyl group; lower alkoxycarbonyl(lower)alkylcarbamoyl group; lower alkylcarbamoyloxy(lower)alkylcarbamoyl group, di(lower)alkylcarbamoyl group; N-{hydroxy(lower)alkyl}(lower)alkylcarbamoyl group; N-{hydroxy(lower)alkyl}(lower)alkylcarbamoyloxy(lower)alkylcarbamoyl group; lower alkylcarbamoyloxy(lower)alkenoyl group; N-{heterocyclic carbonyloxy(lower)alkyl}(lower)alkylcarbamoyl group; cyclo(lower)alkylcarbamoyl group; arylcarbamoyl group; haloarylcarbamoyl group; protected carbamoyl group; lower alkylthiocarbamoyl group; heterocyclic carbamoyl group; ar(lower)alkenoyl group; lower alkoxycarbonyl group; heterocylic carbonyl group which may have lower alkyl group, hydroxyl group, hydroxy(lower)alkyl group, lower alkoxy(lower)alkyl group, or lower alkoxycarbonyl group; lower alkyl group; carboxy(lower)alkyl group; protected carboxy(lower)alkyl group; ar(lower)alkyl group which may have halogen atom or lower alkoxyl group; heterocyclic(lower)alkyl group; lower alkylcarbamoyl(lower)alkyl group; hydroxy(lower)alkenoyl group; acyloxy(lower)alkenoyl group or diacyloxy(lower)alkenoyl group; R² represents lower alkoxyl group, and R³ represents the formula:

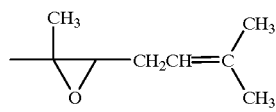

the formula:

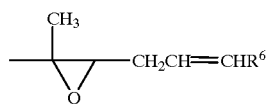

(wherein R⁶ represents protected carboxyl group), the formula:

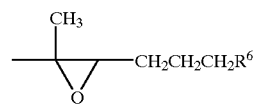

(wherein R⁶ represents the same as described above), the formula:

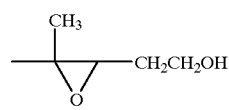

the formula:

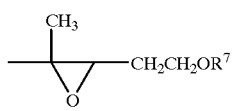

(wherein R⁷ represents protected carboxy(lower)alkyl group or ar(lower)alkyl group which may have halogen atom), or the formula:

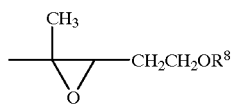

(wherein R⁸ represents acyl group), or a pharmaceutically acceptable salt thereof.

7. The method of claim 6, wherein R¹ represents lower alkylcarbamoyl group, R² represents lower alkoxyl group, and R³ represents the formula:

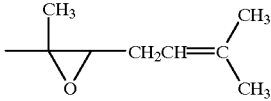

in general the formula of oxaspirooctane derivative (I).

8. The method of claim 7, wherein the oxaspirooctane derivative (I) is 6-methylcarbamoyloxy-5-methoxy-4-{2-methyl-3-methyl-2-butenyl)oxiranyl}1-oxaspiro{2.5}octane.

9. The method of claim 6, wherein R¹ represents protected carbamoyl group, R² represents lower alkoxyl group, and R³ represents the formula:

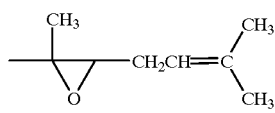

in the general formula of the oxaspirooctane derivative (I).

10. The method of claim 9, wherein the oxaspirooctane derivative (I) is 6-monochloroacetylcarbamoyloxy-5-methoxy-4-{2-methyl-3-(3-methyl-2-butenyl)oxiranyl}-1-oxaspiro{2.5}octane.

11. A method for suppressing retention of carcinomatous ascites in mammals comprising administering to a mammal in need thereof a carcinomatous ascites retention suppression effective amount of an oxaspirooctane derivative of the general formula (I):

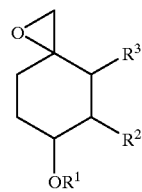

wherein, $R^1$ represents carbamoyl group; lower alkylcarbamoyl group; hydroxy(lower)alkylcarbamoyl group; lower alkoxy(lower)alkylcarbamoyl group; lower alkylthio(lower) carbamoyl group; lower alkoxycarbonyl(lower) alkylcarbamoyl group; lower alkylcarbamoyloxy(lower) alkylcarbamoyl group, di(lower)alkylcarbamoyl group; N-{hydroxy(lower)alkyl}(lower)alkylcarbamoyl group; N-{hydroxy(lower)alkyl}(lower)alkylcarbamoyloxy(lower) alkylcarbamoyl group; lower alkylcarbamoyloxy(lower) alkenoyl group; N-{heterocyclic carbonyloxy(lower)alkyl}(lower)alkylcarbamoyl group; cyclo(lower)alkylcarbamoyl group; arylcarbamoyl group; haloarylcarbamoyl group; protected carbamoyl group; lower alkylthiocarbamoyl group; heterocyclic carbamoyl group; ar(lower)alkenoyl group; lower alkoxycarbonyl group; heterocyclic carbonyl group which may have lower alkyl group, hydroxyl group, hydroxy(lower)alkyl group, lower alkoxy(lower)alkyl group, or lower alkoxycarbonyl group; lower alkyl group; carboxy(lower)alkyl group; protected carboxy(lower)alkyl group; ar(lower)alkyl group which may have halogen atom or lower alkoxyl group; heterocyclic(lower)alkyl group; lower alkylcarbamoyl(lower)alkyl group; hydroxy(lower) alkenoyl group; acyloxy(lower)alkenoyl group or diacyloxy (lower)alkenoyl group; $R^2$ represents lower alkoxyl group, and $R^3$ represents the formula:

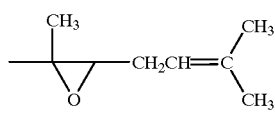

the formula:

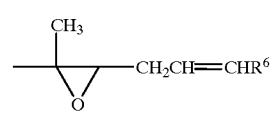

(wherein $R^6$ represents protected carboxyl group), the formula:

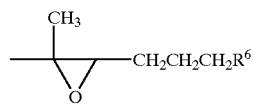

(wherein $R^6$ represents the same as described above), the formula:

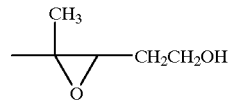

the formula:

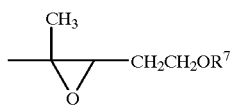

(wherein $R^7$ represents protected carboxy(lower)alkyl group or ar(lower)alkyl group which may have halogen atom), or the formula:

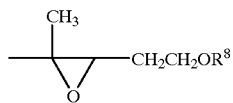

(wherein $R^8$ represents acyl group), or a pharmaceutically acceptable salt thereof.

12. The method of claim 11, wherein $R^1$ represents lower alkylcarbamoyl group, $R^2$ represents lower alkoxyl group, and $R^3$ represents the formula:

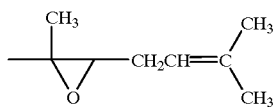

in general the formula of oxaspirooctane derivative (I).

13. The method of claim 12, wherein the oxaspirooctane derivative (I) is 6-methylcarbamoyloxy-5-methoxy-4-{2-methyl-3-methyl-2-butenyl)oxiranyl}-1-oxaspiro{2.5}octane.

14. The method of claim 11, wherein $R^1$ represents protected carbamoyl group, $R^2$ represents lower alkoxyl group, and $R^3$ represents the formula:

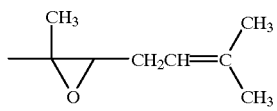

in the general formula of the oxaspirooctane derivative (I).

15. The method of claim 14, wherein the oxaspirooctane derivative (I) is 6-monochloroacetylcarbamoyloxy-5-methoxy-4-{2-methyl-3-(3-methyl-2-butenyl)oxiranyl}-1-oxaspiro{2.5}octane.

* * * * *